(12) United States Patent
Roura

(10) Patent No.: US 7,851,446 B2
(45) Date of Patent: Dec. 14, 2010

(54) USE OF THERAPEUTIC HUMAN ALBUMIN FOR TREATMENT OF ALZHEIMER'S DISEASE

(75) Inventor: Victor Grifols Roura, Barcelona (ES)

(73) Assignee: Grifols, S.A., Barcelona (ES)

( * ) Notice: Subject to any disclaimer, the term of this patent is extended or adjusted under 35 U.S.C. 154(b) by 0 days.

(21) Appl. No.: 12/257,814

(22) Filed: Oct. 24, 2008

(65) Prior Publication Data

US 2009/0111740 A1    Apr. 30, 2009

(30) Foreign Application Priority Data

Oct. 26, 2007    (ES) ................................ 200702831

(51) Int. Cl.
*A01N 37/18*    (2006.01)
*A61K 38/16*    (2006.01)

(52) U.S. Cl. .................. 514/15.2; 514/13.5; 514/1.1

(58) Field of Classification Search .................. None
See application file for complete search history.

(56) References Cited

U.S. PATENT DOCUMENTS

| | | | |
|---|---|---|---|
| 4,900,720 A | 2/1990 | Kotitschke et al. | |
| 5,112,298 A | 5/1992 | Prince et al. | |
| 5,178,603 A | 1/1993 | Prince | |
| 2005/0239062 A1 | 10/2005 | Zlokovic | |

FOREIGN PATENT DOCUMENTS

| EP | 1576955 | 9/2005 |
|---|---|---|
| WO | WO-03/051374 | 6/2003 |
| WO | WO-2004031161 | 4/2004 |
| WO | WO-2004/071524 | 8/2004 |
| WO | WO-2005065069 | 7/2005 |
| WO | WO-2006/005706 | 1/2006 |
| WO | WO-2007/0010435 | 1/2007 |

OTHER PUBLICATIONS

Purves, et al, in: *Neuroscience*. Sunderland (MA). Sinauer Associates, Inc.; c2001.<<http://www.ncbi.nlm.nih.gov/books/bv.fcgi?highlight=hippocampus,emotion&rid=neurosci.section.2041>>Accessed Jan. 14, 2009.
Rossler, et al, 2002. "Stage-dependent and sector-specific neuronal loss in hippocampus during Alzheimer's disease". Acta Neuropathol (2002) 103:363-369.
McKhann, et al, 1984. "Clinical diagnosis of Alzheimer's disease: Report of the NINCDS-ADRDA Work Group under the auspices of Department of Health and Human Services Task Force on Alzheimer's Disease", Neurology 34:939-944.
Folstein, et al, 1975 "Mini-Mental State". J Psychiat Res 12:189-198.
Rosen, et al., 1984. "A New Rating Scale for Alzheimer's Disease", Am J Psychiatry 141: 1356-1364.

*Primary Examiner*—Olga N Chernyshev
(74) *Attorney, Agent, or Firm*—Buchanan Ingersoll & Rooney PC

(57) ABSTRACT

The present invention relates to the use of therapeutic human albumin for the preparation of a drug for the treatment of patients suffering from cognitive disorders. In particular, the invention relates to methods of treating patients suffering from cognitive disorders, in which the mode of administration of the drug comprises the administration to the patient for a minimum of three successive times of a therapeutically effective amount of human therapeutic albumin by plasma exchange and/or intravenous perfusion, independently of the content of Aβ in the patient's blood.

6 Claims, 3 Drawing Sheets

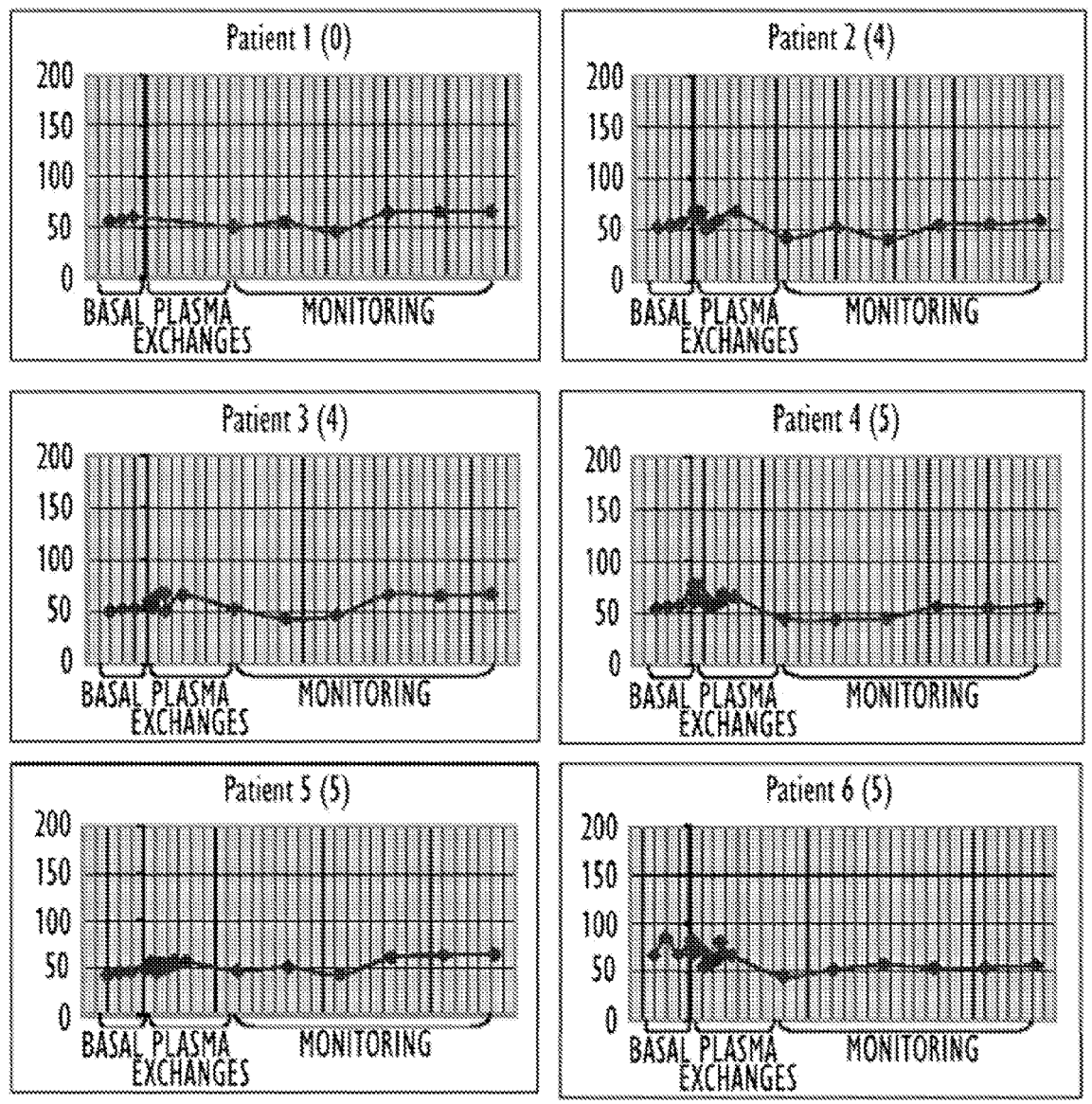

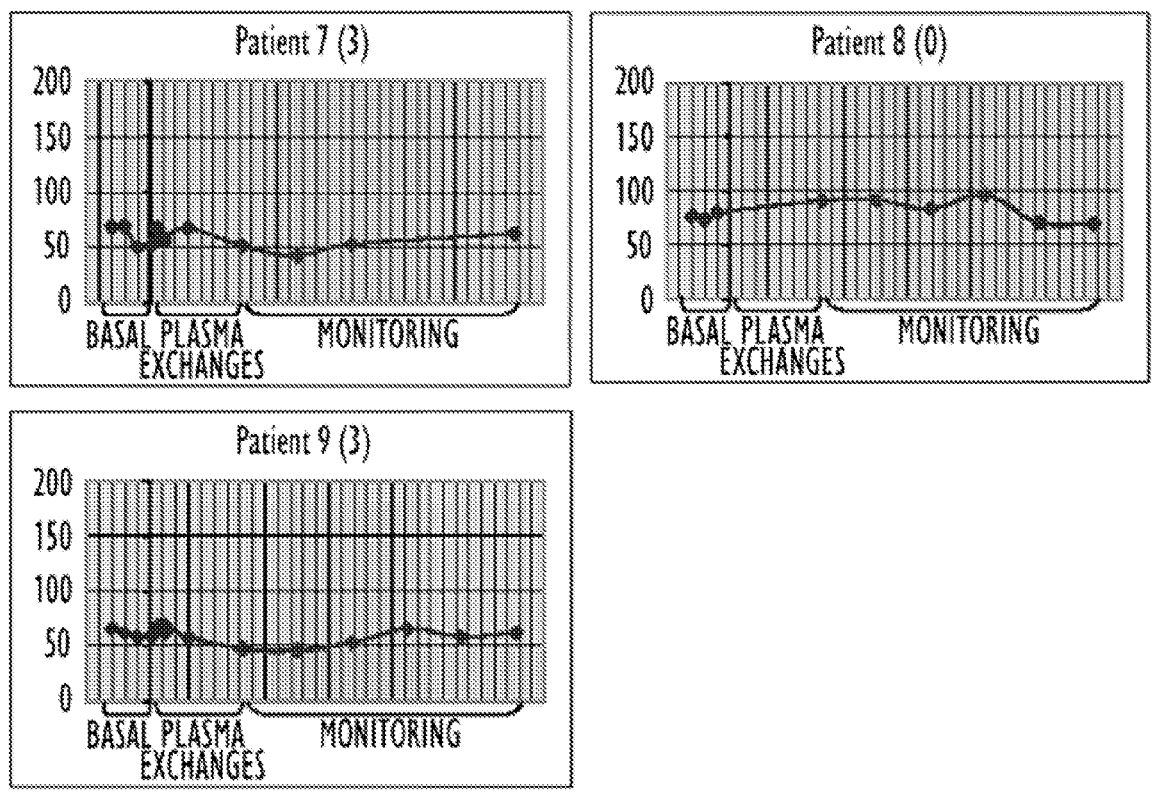

USE OF THERAPEUTIC HUMAN ALBUMIN FOR TREATMENT OF ALZHEIMER'S DISEASE

This application claims the benefit of priority to Spanish Patent Application No. P200702831 filed Oct. 26, 2007, the disclosure of which is hereby incorporated by reference in its entirety.

FIELD OF THE INVENTION

The present invention relates to the use of therapeutic human albumin for the preparation of a drug for the treatment of cognitive disorders such as Alzheimer's disease. The drug will preferably be for administration to the patient by plasma exchange (therapeutic plasmaphaeresis). At the same time, the present invention will provide the means for the treatment of cognitive disorders in individuals suffering from Alzheimer's disease or of those who are suspected of being suffering from this disease.

The invention is the result of the investigations performed by the inventor, which have resulted in a new use of human therapeutic albumin for treatment preferably by therapeutic plasma exchange which has proved to be effective in the treatment of Alzheimer's disease.

BACKGROUND

Alzheimer's disease is an irreversible cerebral degenerative pathology which affects the nerve cells of the cerebral cortex in a diffuse fashion, and also other adjacent structures such as the Hippocampus. This causes the deterioration of the subject's capacity to control emotions, recognise errors and patterns of behaviour and coordinate movements and memory, which combined are known as dementia. Finally the memory and the higher mental faculties are completely lost.

The hippocampus is a region of the brain situated in the temporal lobe which extends along the whole of the lower part of the inferior horn of the lateral ventricles (it measures about 5 cm). It takes its name from the shape of a "sea horse" which its folds take in the transverse sections of the brain. The hippocampus is formed principally of neurones of the grey matter although it has a thin layer of white matter on the upper surface connected to the lateral ventricles.

Functionally, the hippocampus forms one of the most prominent parts of the limbic system, which plays a preponderant role in the control of the higher functions, especially the emotions [Purves D, Augustine G J, Fitzpatrick D, Katz L C, LaMantia A, McNamara J O and Williams S M, in: *Neuroscience*. Sunderland (MA). Sinauer Associates, Inc.; c2001].

It is at present considered that the hippocampus is one of the most intensely affected cerebral regions in Alzheimer's disease (loss of volume) and several reports suggest that the loss of hippocampus neurones is correlated to the loss of memory which is observed in this disease [Rössler M, Zarski R, Bohl J. and Ohm TG. *Stage-dependent and sector-specific neuronal loss in hippocampus during Alzheimer's disease*. Acta Neuropatol (2002) 103:363-369].

In Alzheimer's disease specific changes also occur in the cerebral structures, amongst which is a tangling of the neuron fibrils, known as neurofibrillar bundles, and an extracellular protein deposit in the form of the so-called beta-amyloid (A$\beta$) peptide plaque. These neurofibrillar bundles and beta amyloid plaques have been connected with the development of the disease. In spite of this the cause of the disease is unknown, although the commonly accepted theory associates the development of the disease with a deposition of the beta-amyloid (A$\beta$) peptide.

The neurofibrillar bundles contain, inter alia, residues of damaged microtubules, and these microtubules form a structure allowing the flow of nutrients through the neuron. A fundamental component of these bundles is the aberrant form of the so-called tau protein, which in its "normal" form contributes to the formation of a suitable structure of microtubules. Instead, an anomalous tau protein blocks the action of a healthy tau protein. A$\beta$ is a protein which accumulates in the form of neuritic plaques which appear surrounded by the residues of destroyed ramifications of the affected neurons. A$\beta$ is in turn a fragment of the so-called amyloid precursor protein (APP) which upon being cut by determined enzymes can give rise to different types of A$\beta$, hence this protein has a certain heterogeneity in its sequence of amino acids, the A$\beta$40 form being the most common in normal subjects. The A$\beta$42 ("long A$\beta$") form shows a greater tendency to aggregate, and there is a theory which suggests that it could be responsible for initiating aggregation into plaques.

High A$\beta$ levels in the Cerebrospinal Fluid (CSF) are associated with low levels of acetylcholine, which is an important neurotransmitter, or chemical messenger which transmits signals between the cerebral neurons. Acetylcholine forms part of the cholinergic system, vital for memory and learning, which is progressively destroyed in Alzheimer's disease patients.

As in this disease a strong synaptic loss and a profound change in the cholinergic and glutamatergic neurotransmitter systems occur, and the current treatment attempts to mitigate the synaptic pathology with the drugs today in use, the anticholinesterasics and NMDA glutamatergic antagonists. These cholinergic and antiglutamatergic drugs could retain their indication for the future because, as this disease is so molecularly complex, adjusted polytherapy can be necessary in each developing stage in which the process is encountered.

In addition, the current investigation is fundamentally centred on drugs which try to halt the progression of the disease from the start. Antiamyloid agents are used, which effectively impede the excessive production of A$\beta$, its aggregation and deposit or which clean accumulations of A$\beta$ once they have been formed. Another important target is the agents which avoid phosphorylation and aggregation of tau so as not to form bundles.

There are at present several drugs which are already under clinical trial following these routes of activation, with agents which try to inhibit the formation of APP, as indicated for example in the EP1576955 patent.

Another strategy at present under trial is the use of certain anti-inflammatories, such as flurbiprofen, described in the WO2005065069 patent, which acts by modulating $\gamma$-secretase activity.

The option of inhibiting $\gamma$-secretase is compromised because this enzyme has many other substrata which, if they are also inhibited, can produce side effects.

Another therapeutic possibility which is at present being studied is that of avoiding the conversion of the soluble A$\beta$ into insoluble restructures which form deposits, such as the drug Alzhemed of the Canadian company Neurochem, which opposes the fibrilisation of A$\beta$, inhibiting its deposit.

Moreover, the A$\beta$ does not aggregate spontaneously but depends on metals such as Cu, Fe and Zn. These metals increase in the brain in cases of Alzheimer's disease triggering the precipitation of A$\beta$. The chelating compounds which combine with these metals can correct the aggregation of A$\beta$ and be of therapeutic use in the treatment of Alzheimer's disease, as described in the WO2004031161 document.

The anti-Aβ immunotherapy originated when it was discovered that areas of inflammation appeared around the Aβ deposits and neurofibrillar bundles, in response to these abnormal structures. This gave rise to clinical studies with vaccines based on synthetic Aβ, which even if they acted against the accumulation of Aβ, caused severe side effects, such as the development of serious meningoencephalitis resulting in death in some cases. At present safer and more efficacious agents are being sought.

These mechanisms of action are principally based on blocking the formation of the insoluble form of Aβ, avoiding its deposit or the elimination of the deposits already formed, all of them acting directly on the cerebral tissue. This involves, as we have remarked, a risk of adverse side effects by direct action on the central nervous system.

Another aspect considered in the therapeutic strategy against Alzheimer's disease is, bearing in mind that the production of Aβ is continuous in the brain, its accumulation due to the deficient transfer of the CSF to the blood and the elimination of this could increase the possibility of the deposition of this Aβ in the brain.

Following this line of activity, US 2005/0239062 refers to the therapeutic activity of increasing the transport of the Aβ across the Haematoencephalic Barrier (a mechanism which seems not to function correctly in Alzheimer's disease), acting at the level of specific transporters of this Aβ.

Documents WO 2006/005706 and WO 03/051374 show a mode of peripheral activity, which does not act at the level of the central nervous system or the haematoencephalic barrier, but through the blood. In this way the problems of the crossing of the active substances of the haematoencephalic barrier and the serious possibility of adverse side effects on the central nervous system are avoided.

Document WO 2006/005706 discloses a method of extra-corporeal treatment (aphaeresis), eliminating the APP from the plasma (or blood) of the patient by a specific ligand in the aphaeresis device. Aphaeresis is a technique which involves the extracorporeal treatment of the blood, by its extraction, treatment and reinfusion; this, as we shall see, is outside the scope of the present invention.

Document WO 03/051374 is based on the administration to the patient of an agent with affinity for Aβ in blood. This agent does not cross the haematoencephalic barrier but upon the isolation and reduction of Aβ in the blood the concentration of this Aβ in the cerebrospinal fluid (CSF, the fluid which bathes the brain) will be reduced. The agents claimed by this patent would be modified in order to speed up their metabolisation, which would facilitate the elimination of Aβ from the blood.

US 2007/0010435 shows a method for the treatment of amyloid diseases by the elimination of amyloid peptides from the bodily fluids, based on the administration of a compound capable of uniting with the amyloid-beta and its elimination by dialysis or plasma exchange. In a particular realisation it shows the treatment of the blood or plasma "ex vivo", by dialysis or haemofiltration for example, and reinfusion to the individual. As we have seen, WO 2006/005706 also showed this extracorporeal treatment technique. A particular form of realisation in the elimination of the amyloid-beta from the "ex vivo" blood will be achieved by plasma exchange, without the use of a ligand for amyloid-beta, replacing the patient's plasma by free amyloid-beta plasma. In this patent application (US 2007/0010435, paragraphs 24, 25 and 143) the system of plasmaphaeresis (treatment protocol) and the measure of its efficacy in accordance with the level of amyloid-beta in plasma, controlled by taking blood samples before and after plasmaphaeresis are established. The treatment (dialysis or plasma exchange) intervals are in accordance with these data, for the purpose of maintaining a low amyloid-beta level. As indicated in paragraph 32 of US 2007/0010435, the "treatment" refers to a method of reducing the amyloid-beta concentration or amount in blood or CSF.

To summarise, US 2007/0010435 shows two general treatment types, an "in vivo" treatment by the infusion of a specific amyloid-beta ligand, with an affinity for the same greater than that of the plasma proteins or an "ex-vivo" treatment where it is not in contact in the individual with the specific amyloid-beta ligand or including the plasma exchange, where the use of ligands is not required. As is deduced from the description and examples included in this US 2007/0010435, this is based on the concept of reducing the amyloid-beta content in the patient's blood, expressly indicating (example 6, paragraph 143) that the procedure is performed monthly, by analysing blood samples in order to deduce the total Aβ levels, determining the precise intervals between treatments from the information resulting from analysing the Aβ content in blood. However, as will be explained below in more detail, the inventor, after extensive investigations, reached the conclusion that this focus is erroneous since the plasma exchange does not in practice reduce the Aβ concentration or amount in the blood, so that the performance of the procedure provided in US 2007/0010435 is based on a mistaken supposition, since by not in practice varying the Aβ concentration in blood after plasma exchange treatments, basing the treatment on the Aβ concentration in the blood would be a mistake on the part of the clinic.

It is therefore clear that given the considerable importance of the possible treatment of Alzheimer's disease, it is still necessary to find new methods for the treatment of this disease. For this reason, the inventor decided to investigate new ways, discovering that plasma exchange with albumin would allow significant advances to be made in the treatment of Alzheimer's disease, surprisingly, independently of the amyloid-beta concentration in the plasma or blood.

Therapeutic plasma exchange (TPE) or plasmaphaeresis is used to eliminate pathogenic substances from the patient's blood. The terminology relating to therapeutic plasma exchange (TPE) and plasmaphaeresis is not uniform in the specialised literature. As it is used in this description, the term therapeutic plasma exchange refers to the substitution of a patient's plasma by a medium of substitution. During the process the normal constituents of the plasma are eliminated together with pathogenic substances. For a general explanation of therapeutic plasma exchange and the involvement of albumin in it, see U.S. Pat. No. 4,900,720, which is incorporated in the present for reference.

Specifically, TPE involves the elimination of plasma in the patient, replacing it with another solution to simultaneously preserve the normovolaemic state, that is, osmotic balance. Replacement by albumin or other colloids, fresh frozen plasma (FFP) and crystalloids has been used for TPE. The solution and volume used will depend on the intensity (frequency) of plasmaphaeresis. In the case of albumin solutions at 4% (p/v), 5% (p/v) and other concentrations up to 25% (p/v) have been used, if necessary, after dilution in physiologically compatible solutions. The basic aim of TPE is to eliminate toxic substances from the plasma, which can be: autoantibodies, alloantibodies, immune complexes, proteins or toxins.

Several documents describe devices for performing TPE. See for example U.S. Pat. Nos. 5,112,298 (Simplified method of separation of fluid and devices to be used for various aphaeresis processes, including plasmaphaeresis); and U.S.

Pat. No. 5,178,603 (Method and system for adaptively controlled extraction/infusion of a fluid such as blood to a source of fluid or from the latter, such as blood vessel) which is incorporated in this for reference.

The clinical efficacy of TPE depends on many factors including the volume of interchange, the number and frequency of sessions, the nature of the replacement solution and the separation technique.

When TPE is performed with a replacement liquid different from FFP, a considerable depletion of the plasma proteins occurs, special importance being given to immunoglobulins and coagulation factors. Haemorrhagic conditions caused by the fall in the coagulation factors cannot therefore be ruled out. In extreme cases, it is advisable to administer these coagulation factors. Thrombotic conditions can also be caused by the same mechanism. Hypotension is one of the most frequent complications in TPE. It is considered that the risk of adverse side effects is high when the extracorporeal volume is greater than 15% of the total volaemia. This risk can be minimised with meticulous attention to the water balance and with due monitoring of patients. Less frequently, conditions of cardiac insufficiency, myocardial ischaemia, pulmonary oedema and respiratory distress have also been described.

The use of this therapeutic procedure is restricted to very definite indications and only US 2007/0010435 has associated it with the elimination or reduction of amyloid-beta. As has been indicated above said patent application is limited to describing this possibility, but, as is observed in this application, the possible usefulness of this plasma exchange is a mere theoretical speculation and the concept and methods of control of administration provided in this Patent lead us to erroneous conclusions since as has been indicated and will be seen below from the trials performed, plasma exchange does not involve any reduction in the concentration or amount of amyloid-beta in the blood.

From the investigations carried out by the inventor, and as can be verified in the examples of this patent, plasma exchange does not provide the effect of reduction of amyloid-beta in the blood of patients suffering from cognitive disorders such as Alzheimer's disease.

BRIEF DESCRIPTION OF THE DRAWINGS

FIG. 1 shows the results of the concentrations of A$\beta$42 in plasma for each patient (FIG. 1A=Patients 1-6; FIG. 1B=Patients 7-9) in the Example described herein.

DETAILED DESCRIPTION

Figure 2:
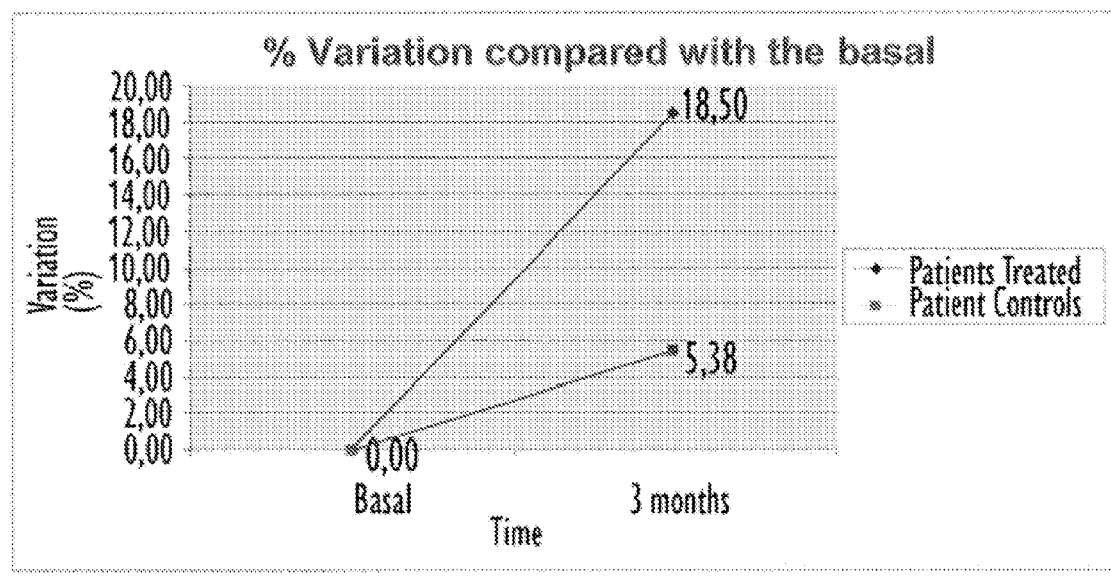
FIG. 2 shows the percentage of variation of the hippocampus volume (average) compared with the basal value is compared, over the trial (3 months) in the Example described herein.

The present invention relates to the use of therapeutic human albumin for the preparation of a drug for the treatment of patients suffering from cognitive disorders, in which the mode of administration for the drug comprises the administration to the patient for a minimum of three successive times, of a therapeutically effective amount of human therapeutic albumin by means of plasma exchange and/or intravenous perfusion, independently of the content of A$\beta$ in the patient's blood.

The present invention also provides a therapeutic method for the treatment of patients suffering from cognitive disorders.

From the investigations performed by the inventor, surprisingly, independently of the concentration of amyloid-beta in the blood, when therapeutic plasma exchange and replacement of the normovolaemic volume albumin with a determined frequency of treatment are used, an increase in the volume of the hippocampus occurs, which is associated with an improvement in the clinical symptoms of Alzheimer's disease. This can be due to factors that are soluble and permeable to the blood-brain barrier; nevertheless, the scope of the claims must not be limited by any specific theory.

Therapeutic plasma exchange with albumin can be used as a method for the treatment of cognitive disorders. One use provides a method for the treatment of a patient who suffers from cognitive disorders or in whom these have been diagnosed, comprising performing therapeutic plasma exchange on the patient, the frequency of which involves effective therapeutic substitution with albumin.

As used in this description, the term "cognitive disorders" refers to degenerative cerebral pathologies including Alzheimer's disease.

The method of treatment does not depend on a specific, plasma or CSF level of concentration of amyloid-beta peptide (titration), nor does it depend on its relative reduction. The advantages of the method are demonstrated by the increase in the volume of the hippocampus. The therapeutic plasma exchange of the invention increases the volume of the hippocampus, expressed as corrected Volume of the Hippocampus which equals: (Left Hippocampus Volume+Right Hippocampus Volume)/Cerebral Volume×1000.

This method establishes a specific regimen of therapeutic plasma exchange to increase the volume of the hippocampus. As with other uses, albumin is present in the medium of interchange at 4% up to 25% weight/volume. In some uses, albumin is present approximately from 4.5% to 5.5% weight/volume.

Another additional use is for therapeutic plasma exchange to be used prophylactically in patients diagnosed with cognitive disorders, who are in the initial stages of the disease, or in those where other risk factors for the development of cognitive disorders are identified. In these cases, the desired therapeutic effect may not be limited to an increase in volume of the hippocampus, but to a prevention of the reduction of its volume.

Repetition of plasma exchange is indispensable. In general, a minimum of 3 exchanges are necessary to provide an increase in volume of the hippocampus.

EXAMPLE

A test for patients with Alzheimer's disease has been devised and performed for the purpose of determining whether an exhaustive plasma exchange regimen (more than 3 times or 3 times in 3 weeks) can modify cognitive and behavioural deterioration.

Efficacy and safety variables are investigated in this test. The variation in cognitive and behavioural deterioration and in the volume of the hippocampus is measured as efficacy indicators by different scales.

The test sample is focused on patients with mild-moderate Alzheimer's disease, with Mini Mental Status Examination (MMSE) between 20-24 (NINCDS-ADRDA Criteria: Neurology 1984; 34:939-944).

The test procedure comprised using an exhaustive plasma exchange regime, which necessarily involves the use of albumin as a replacement solution for the plasma, in this example in the 5% concentration (p/v) due to the convenience of not needing prior dilution into physiologically compatible substances, but any other initial concentration of albumin could also have been used, subject to being adjusted to physiologically compatible concentrations for intravenous use. The albumin used is for therapeutic use which meets European Pharmacopoeia specifications but any other albumin composition would be useful in this invention.

Between 3 and 5 therapeutic plasma exchanges were performed over 3 weeks with a volume of exchange similar to the plasma volaemia of the patient, in this example at a speed of 60-100 ml/min.

Finally, 9 patients were included in the trial 2 of whom were controls; that is to say, did not receive any treatment. The remaining 7 patients received 3, 4 or 5 plasma exchanges.

The experimental stage of the trial comprised a recruitment period, a plasma exchanges period, a monitoring period of 5 months (1 appointment/month) and a final appointment 6 months after the exchanges were completed. In all these appointments different additional monitoring means were used: extractions of plasma and CSF in order to quantify different forms of beta-amyloid peptide, a cognitive assessment by neuropsychological tests and neuroimaging (Nuclear Magnetic Resonance and Tomography by Single Photon Emission). The volume of the hippocampus was assessed by Nuclear Magnetic Resonance.

method for grading the cognitive state of patients for the clinician. J Psychiatr Res 1975; 12:189-198) and to the Adas-Cog (Rosen W G et al. A new scale for Alzheimer's disease. Am J Psychiatry 1984; 141:1356-1364).

MMSE is a test which assesses cognitive changes. The score goes from 0 to 30 with 30 being the highest score.

The Adas-Cog test is a test specifically designed to assess the severity of the fundamental cognitive changes characteristic of Alzheimer's patients. The total score goes from of 0 to 70 with 0 being the highest score.

In tables 1 and 2, which are attached below, the results obtained by the patients in these tests are summarised, by taking the differences in score between the basal assessments (before the plasma exchanges) and monitoring at 3 and 6 months (after the plasma exchanges).

Table 1: MMSE Cognitive Test.

The differences are shown between the cognitive assessments of monitoring at 3 and 6 months compared with the basal. (The result is better when the differences are more positive)

TABLE 1

| MMSE Test | Control Patient 1 | Control Patient 8 | Patient 7 | Patient 9 | Patient 2 | Patient 3 | Patient 4 | Patient 5 | Patient 6 |
|---|---|---|---|---|---|---|---|---|---|
| No. of Plasma Exchanges | 0 | 0 | 3 | 3 | 4 | 4 | 5 | 5 | 5 |
| Monitoring at 3 months compared with the basal | −2 | 1 | 1 | −2 | −2 | 2 | 5 | 4 | 6 |
| Monitoring at 6 months compared with the basal | −7 | 2 | 4 | −6 | 1 | 2 | 1 | 6 | 5 |

Table 2: Adas-Cog Cognitive Test.

The differences are shown between the cognitive assessments of monitoring at 3 and 6 months compared with the basal.

(The result is better when the differences are more positive)

TABLE 2

| Adas Test | Control Patient 1 | Control Patient 8 | Patient 7 | Patient 9 | Patient 2 | Patient 3 | Patient 4 | Patient 5 | Patient 6 |
|---|---|---|---|---|---|---|---|---|---|
| No. of Plasma Exchanges | 0 | 0 | 3 | 3 | 4 | 4 | 5 | 5 | 5 |
| Monitoring at 3 months compared with the basal | 1 | −2 | 0 | −1 | 5 | −8 | −1 | −5 | −6 |
| Monitoring at 6 months compared with the basal | 5 | 0 | −3 | 5 | −2 | −1 | 2 | −1 | −5 |

Results: Of the 7 patients treated, 3 received 5 plasma exchanges (patients 4, 5 and 6), 2 received 4 exchanges (patients 2 and 3) and 2 received 3 exchanges (patients 7 and 9).

The results of the concentrations of Aβ42 in plasma are shown in FIGS. 1A and 1B, expression in pg/ml, analysed with the Innotest Aβ42 kit of Innogenetics. The results are shown by patient, for the 7 patients treated and the 2 control patients (0 exchanges). The number of exchanges performed appears in brackets.

The results show no variation in Aβ42 values compared with the basal values (recruitment period). Therefore this parameter is not useful for establishing a plasmaphaeresis treatment regimen, or to determine its success.

Assessment of the Neuropsychological Tests:

As regards cognitive assessment by neuropsychological tests, different tests were used for which we refer to the MMSE (Folstein M F et al. "Mini-mental state", a practical In Table 1, we can observe that patients who received 4 or more plasma exchanges had an improved MMSE score (differences of 1 to 6 positive points).

In Table 2 an improvement in the score can also be observed (difference of more than 2 negative points) for the Adas-Cog test.

It should be emphasised that a neuropsychological assessment is considered very relevant in some patients and is reflected in the MMSE with positive differences of up to 5 and 6 points (patients 5 and 6, who had 5 plasma exchanges).

Therefore, a considerable clinical improvement is observed from the cognitive results of the neuropsychological tests (MMSE and Adas-Cog) on patients who received 4 or more plasma exchanges. In addition, the improvement seems more marked in patients who received 5 exchanges.

As a result, a new therapy is described in the present invention using plasma exchange for persons suffering from cognitive disorders, especially Alzheimer's disease, or for those who are suspected to be suffering from this disease. The plasmaphaeresis regimen must be intense (exhaustive) and cannot be controlled by means of amyloid-beta plasma values and involves the replacement of the plasma volume with therapeutic solutions which contain human albumin. The efficacy and repetition of the treatment is established by neuroimage and neuropsychological assessment. A therapeutic treatment is also described for persons suffering from Alzheimer's disease or patients diagnosed with this disease who are in the initial stages of the disease, or in those in which other risk factors are identified for the development of the disease, including giving the patient a plasma exchange with albumin in a series of sessions, preferably more than three, over a period of between several days and several weeks, preferably a maximum of approximately three weeks. Additional advantages may be obtained by using a similar volume of exchange to the patient's plasma volume.

Additional advantages may also be obtained by using albumin with a capacity for linking substances greater than the formulation according to the European Pharmacopoeia, since it is possible that the symptoms of cognitive disorders, including Alzheimer's disease, are mediated by substances capable of uniting with albumin plasma, such as, for example, the metals previously mentioned (Cu, Fe and Zn) on which the aggregation of amyloid Beta in the brain can depend. This albumin with greater linking capability could be obtained, for example, as shown in WO 2004/071524, which is incorporated in the present as reference. The use of stabilising agents which trigger the reduction of its linking ability is avoided in the formulation of this albumin.

The investigations and implementations which have been described are not limitative. Several changes and alterations based on what has been described in the present descriptions and claims are within the capabilities of the experts on the subject and provision is made for them to be included within the scope of this Patent.

All publications, patents, articles, and other references cited and/or discussed in this specification are incorporated herein by reference in their entirety and to the same extent as if each reference was individually incorporated by reference.

The invention claimed is:

1. A method of treating a patient suffering from Alzheimer's Disease, comprising
   administering to said patient a therapeutically effective amount of human therapeutic albumin by plasma exchange in a hippocampus-volume-increasing regime and independently of the content of Aβ in the patient's blood
   and assessing the patient's hippocampus volume.

2. The method of claim 1, wherein the human therapeutic albumin is administered in the form of a solution for plasma exchange.

3. The method of claim 1, wherein the plasma exchange is repeated at least three times over a period of three weeks.

4. The method of claim 1, wherein the plasma exchange is achieved with a volume of exchange similar to the patient's plasma volume.

5. The method of claim 1, wherein the therapeutic human albumin is at a concentration between 4% (p/v) and 25% (p/v).

6. The method of claim 5, wherein the therapeutic human albumin is at a concentration between 4.5% (p/v) and 5.5% (p/v).

* * * * *